United States Patent [19]

Coan et al.

[11] Patent Number: 5,110,913
[45] Date of Patent: May 5, 1992

[54] ANTIBODY PURIFICATION METHOD

[75] Inventors: Michael Coan, El Cerrito; Vivian W. Lee, Richmond, both of Calif.

[73] Assignee: Miles Inc., Elkhart, Ind.

[21] Appl. No.: 528,523

[22] Filed: May 25, 1990

[51] Int. Cl.$^5$ .............................. C07K 3/12; C07K 3/22
[52] U.S. Cl. .............................. 530/388.23; 530/387.1; 530/412; 530/415; 530/416; 530/388.1; 530/389.2
[58] Field of Search ............... 530/387, 412, 415, 416, 530/417

[56] References Cited

U.S. PATENT DOCUMENTS 4,234,570 11/1980 Kanbayashi et al. ............... 532/395
4,771,128 9/1988 Ferris et al. ....................... 424/85.91

FOREIGN PATENT DOCUMENTS 1247096 10/1989 Japan.

OTHER PUBLICATIONS

Yost et al., Practical Liquid Chrometography-An Introduction, (Perlin-Elmes, Corp.) pp. 113-115 (1980).
Gill, Electrophoresis, vol. 6, pp. 282-286 (1985).
Fagerstam et al., J. Chromatog. vol. 266, pp. 523-532 (1983).
Marston, Biochem. J., vol. 240, pp. 1-12 (1986).

*Primary Examiner*—F. T. Moezie
*Assistant Examiner*—Andrew G. Rozycki
*Attorney, Agent, or Firm*—Elizabeth F. Enayati; James A. Giblin

[57] ABSTRACT

Method of purifying a protein from a solution of substances comprising the steps of passing the solution through an ion exchange material at a pH which facilitates binding of the protein of interest, washing the bound protein at a different pH at which the bound protein does not elute but which the free protein would not bind to the ion exchange material, and then eluting the protein at a pH which facilitates elution. Method is especially useful in purification of antibodies such as antibodies to tumor necrosis factor.

6 Claims, No Drawings

ANTIBODY PURIFICATION METHOD

BACKGROUND OF THE INVENTION

1. Field

This disclosure is concerned generally with a method of purifying proteins and specifically with a three step method involving pH adjustments to purify the protein without the use of precipitation agents or salt solutions.

2. Prior Art

Current methods for purification of proteins include using precipitation agents such as salts or non-salt substances such as polyethylene glycol (PEG). Unfortunately, in many cases the protein yields are less than desired. The methods are often time consuming and often require the use of specialized equipment such as large centrifuges. Also, it is often difficult to scale up a precipitation method and even if this can be done dissolution of the resulting precipitate can be slow and is not always complete.

Another common method for purifying proteins includes passing a protein-containing solution over or through an appropriate ion exchange material at a solution pH which facilitates binding of the desired protein. This is commonly followed by a washing step and an elution step at a different ionic strength or pH which facilitates the release of the protein. See, for example Lamy, J. et al, Arch Biochem. Biophys. 193 pp 140–149 (1979), showing that protein can be eluted from DEAE Sepharose ® by using a descending pH gradient. In general, altering the pH of a protein towards its isoelectric point causes it to lose net charge and elute from an ion exchanger. Elution of materials from ion exchangers by pH change and ionic strength change is described more fully in Morris et al, *Separation Methods in Biochemistry* Pittman and Sons, London, 1964. See also Robert Scopes, *Protein Purification,* Springer-Verlag, New York, N.Y., 1982. At page 85, the author points out that the use of a change in buffer pH is generally not very successful (for protein purification).

We have now found that by slightly modifying the above ion exchange/pH method, we can purify a protein such as a monoclonal antibody in a relatively simple manner that avoids protein loss commonly associated with existing protein purification methods, especially methods based on the use of solutions of increasing ionic strength. Details of our method are described below.

SUMMARY OF THE INVENTION

Our method of purifying a protein from an aqueous solution containing impurities comprises three essential steps. In the first step, the solution is contacted with an ion exchange material at a solution pH which facilitates binding of the desired protein (first pH). Other substances (impurities) may also be bound during this step. In the next step the exchange material to which the protein is bound is washed with a solution having a different pH which does not elute the protein (second pH). This pH is one which does not facilitate binding of the unbound protein to the ion exchange material but, for some reason, does not facilitate elution of the already bound protein. In the third step, the protein is eluted with a solution having a pH which facilitates protein elution (third pH).

In the preferred embodiment, the protein is an antibody. In the examples below, the method of this disclosure is illustrated using a monoclonal antibody that specifically binds to a substance known as tumor necrosis factor or TNF. In those examples we found that best results could be obtained by binding, washing and then eluting the antibody at three distinct and increasing values of pH.

SPECIFIC EMBODIMENTS

Our disclosure is further illustrated in the examples below in which we purified anti-TNF antibodies expressed from a sub-clone of a deposited cell line having an ATCC Accession No. HB9736. This cell line is described further in patent application Ser. No. 220,206, filed Jul. 18, 1988, incorporated herein now EPO Application No. 0351789.

The improved purification method of this disclosure was discovered while trying to find a way to reduce protein loss that accompanied the use of a precipitation step to purify the monoclonal antibodies to TNF in a clarified (filtered) tissue culture fluid (TCF).

In the TCFs we worked with, the major protein components were the anti-TNF monoclonal antibodies and human albumin, the albumin being present to stabilize the cells of the original (non-clarified) TCF. It had been found particularly difficult to separate albumin from the anti-TNF because of the similarity of their isoelectric points (only 1.5 pH unit difference). Other antibodies are generally easier to separate from albumin because they have a higher isoelectric point (more than 2.0 pH units). As used herein, a significant difference in isoelectric point between human albumin and an antibody, especially a monoclonal antibody, refers to a difference of more than about 2.0 pH units. Having similar isoelectric points means that the difference is less than 2.0 pH units.

We decided to try to replace an unsatisfactory PEG precipitation step with a cation exchange process even though that type of process is not more commonly used for protein purification.

The initial process we used was a fairly standard ion exchange method. That is, at a particular pH and ionic strength we equilibrated a cation exchange column. The ion exchange matrix was S-Sepharose ® which is sulphopropyl surface modified agarose supplied by Pharmacia. The aqueous feed solution (clarified TCF) containing the desired protein was adjusted to the same conditions (pH 4.6, 0.01M sodium acetate) and applied to the column. TCF is the harvest fluid from the cell fermenter. It contains carbohydrates, salts, amino acids, proteins, other cell growth factors, and cells. Clarified TCF has had the cells removed by filtration or some other means. The clarified TCF may be concentrated. We determined the capacity of the column at these conditions and then loaded it to capacity or below. Then, after washing the column with equilibration buffer, the column was eluted, as is typical in ion exchange, by increasing ionic strength. In this case, the conditions were pH 4.6, 0.01M sodium acetate, 0.27 NaCl (i.e. the salt concentration was raised).

Using that technique, the recovery of antibody was >85% with about 15% purity. The next step in this process would have been to use an anion exchange material (e.g., Q-Sepharose ®) for further purification.

It then occurred to us that the elution of the S-Sepharose ® column with a high salt concentration created the necessity of adding a new step (salt reduction or removal) where more protein loss would be expected to occur. This would be undesirable.

Instead of following the above elution method (changing ionic strength), we decided to consider conditions of washing and elution which did not increase the ionic strength but, instead, increased the pH.

In our particular examples, we surprisingly found a set of conditions which would enable much of the impurities (mostly albumin in our examples) to be washed off. In another step, by raising the pH again, we were able to elute the antibody. Thus, in our examples, we were able to find that the anti-TNF should be loaded at an initial value, then washed at a different pH value (in this case higher) and then eluted at yet a third pH value which in this case was the highest.

Surprisingly, we found that if the column was equilibrated and loaded at the intermediate pH, little or no binding of the protein occurred. Although the exact mechanism is not clear, it is thought that conformational changes in the protein at different pH conditions may affect binding. In the case of our examples, it is thought that the lowest pH brings about a conformational or conformational change of the antia-TNF which facilitates binding to the ion exchange matrix. At the intermediate pH, the unbound protein may be in a conformation in which the binding sites are blocked due to a conformational change caused by that pH. If, however, the anti-TNF is already bound to the matrix, the conformational change caused by the intermediate pH may not be possible.

As used herein, the expression different pH, when applied to the intermediate washing step of this disclosure and the claims below, refers to a pH at which a protein (such as the anti-TNF monoclonal antibodies of the examples below) will not bind to an ion exchange material (such as S-Sepharose ®) if in the free or unbound state but which will not elute from the same ion exchange material if already bound to it.

EXAMPLE 1

An S-Sepharose ® (Pharmacia) column was equilibrated with 0.01M sodium acetate at pH 4.6. The anti-TNF containing solution (TCF) was then applied to the column as next described. The solution was diluted with water (approximately 1 part water to 2 parts TCF). The pH of the diluted TCF was adjusted to pH 4.6 with 1M acetic acid. The absorbance at 280 nm ($A_{280}$) was measured and 20 $A_{280}$ units were applied per mL of column. In these examples, we define a protein concentration of one unit per mL as having an $A_{280}$ of 1. The column was washed with the equilibration buffer until the eluting absorbance returned to baseline. The column was then washed with buffer of 0.01 sodium acetate, 0.05M sodium chloride, pH 5.5. Some proteins eluted, and the column was washed until the $A_{280}$ returned to baseline. In the final step, the antibodies were eluted at a solution pH of 6.5. The antibody recovery was 90% with a purity of 30%.

EXAMPLE 2

The same starting clarified TCF as in Example 1 was used. This time, however, the S-Sepharose ® column was equilibrated with 0.01 sodium acetate, 0.05M NaCl, pH 5.5. Also, the TCF was diluted as in Example 1, but was then adjusted to pH 5.5 with 1M acetic acid. The column loading was the same as described in Example 1. The column was washed until the absorbance at 280 nm returned to baseline. The elution was as in Example 1. The recovery of antibody was only 10%. The remaining antibody was accounted for in the unbound fractions.

Given the above disclosure, it is thought that variations will occur to those skilled in the art of protein purification. Accordingly, it is intended that the above examples should be construed as illustrative only and that the scope of the invention of this disclosure should be limited only to the following claims.

We claim:

1. A method of purifying a murine antibody in an aqueous solution comprising the steps of
   (a) binding the antibody to an ion exchange resin at a first pH for the aqueous solution which facilitates antibody binding;
   (b) washing the bound antibody at a second different pH for the wash solution which does not elute the antibody; and
   (c) eluting the antibody at a third pH for the elution solution which facilitates elution, the above purification being done without changes in ionic strength among the solutions of steps (a), (b) and (c).

2. The method of claim 1 wherein the antibody binds tumor necrosis factor.

3. The method of claim 2 wherein the antibody is bound to the ion exchange material at a pH of about 4.6, the washing step is at a pH of about 5.5; and the elution step is at a pH of about 6.5.

4. In a method of purifying an antibody using an initial step at a pH to bind the antibody to an ion exchange material resin and a final step at another pH to elute the antibody, the improvement comprising an intermediate wash step at a different pH which permits the elution of impurities without elution of the antibody and without any change in the ionic strengths of any solutions used for the initial, intermediate and final steps.

5. The method of claim 4 wherein the steps use a sequence of increasing pH in going from the initial to the final step.

6. The method of claim 5 wherein the antibody binds tumor necrosis factor.

* * * * *